United States Patent [19]

Fujii et al.

[11] Patent Number: 5,762,954
[45] Date of Patent: Jun. 9, 1998

[54] ISOSORBIDE DINITRATE-CONTAINING PATCH USING A MIXED ADHESIVE

[75] Inventors: Takao Fujii, Hino; Makoto Iwata, Tokyo; Minoru Furuya, Hino; Michisuke Ohe, Hamura, all of Japan

[73] Assignee: Teijin Limited, Osaka, Japan

[21] Appl. No.: 700,418

[22] PCT Filed: Feb. 28, 1995

[86] PCT No.: PCT/JP95/00318

§ 371 Date: Aug. 28, 1996

§ 102(e) Date: Aug. 28, 1996

[87] PCT Pub. No.: WO95/22970

PCT Pub. Date: Aug. 31, 1995

[30] Foreign Application Priority Data

Feb. 28, 1994 [JP] Japan ............................... 6-029699

[51] Int. Cl.⁶ ............................................ A61F 13/02
[52] U.S. Cl. ............................. 424/448; 424/449
[58] Field of Search .......................... 424/448, 449

[56] References Cited

U.S. PATENT DOCUMENTS

| | | | |
|---|---|---|---|
| 4,849,226 | 7/1989 | Gale | 424/448 |
| 4,956,181 | 9/1990 | Bayer | 424/448 |
| 5,300,291 | 4/1994 | Sablotsky | 424/78.18 |
| 5,474,783 | 12/1995 | Miranda | 424/448 |

*Primary Examiner*—D. Gabrielle Phelan
*Attorney, Agent, or Firm*—Sughrue, Mion, Zinn, Macpeak & Seas, PLLC

[57] ABSTRACT

The present invention provides an ISDN-containing patch that causes minimal occurrence of skin rash and has excellent percutaneous absorption and adhesive strength. The present invention discloses an isorbide dinitrate-containing patch comprising: an adhesive layer formed on a flexible support, wherein said layer comprises an adhesive composition containing adhesive and isosorbide dinitrate, the adhesive being composed of silicone-based adhesive (A) and polyvinyl acetate-based adhesive (B), their weight ratio being A:B=85:15 to 15:85, and the weight ratio of isosorbide dinitrate (C) to the adhesives (A+B) being (A+B):C=90:10 to 60:40.

15 Claims, No Drawings

ISOSORBIDE DINITRATE-CONTAINING PATCH USING A MIXED ADHESIVE

This application is a 371 of PCT/JP95/00318, filed Feb. 28, 1995.

TECHNICAL FIELD

The present invention relates to an isosorbide dinitrate (ISDN)-containing patch. More specifically, the present invention relates to a patch in which an adhesive composition having isosorbide nitrate incorporated in a mixed adhesive comprising a silicone-based adhesive and polyvinyl acetate-based adhesive at a specified mixing ratio is formed on a flexible support and has excellent sustained release properties and good percutaneous absorption.

BACKGROUND ART

Drugs such as isosorbide dinitrate are commonly known to be absorbed percutaneously, and numerous products have already been developed as patches containing these drugs. It is indicated, in, for example, Japanese Unexamined Patent Publication No. 57-116011, that pressure-sensitive adhesives such as silicone-based, rubber-based and acrylic-based pressure-sensitive adhesives are preferable as pressure-sensitive adhesives used in these patches. In addition, at the 5th meeting of the Japan Pharmacology Association (Sep. 26-28, 1989), Okuni, et.al. reported that with respect to patches containing ISDN, in comparing acrylic-based, silicone-based and rubber-based pressure-sensitive adhesives, the percutaneous absorption of these three are roughly equal.

In the above-mentioned Japanese Unexamined Patent Publication No. 57-116011, the application was later published after examination (Japanese Examined Patent Publication No. 4-74329) following amendment by stating that acrylic-based pressure-sensitive adhesives are particularly preferable among various types of pressure-sensitive adhesives.

Namely, in conventional isosorbide dinitrate-containing patches, with respect to the relationship between the percutaneous absorption of ISDN and the pressure-sensitive adhesive, it was considered that acrylic-based pressure-sensitive adhesives are preferable, or that the above-mentioned acrylic-based pressure-sensitive adhesives and rubber-based pressure-sensitive adhesives are equally preferable.

However, a shortcoming of patches is the occurrence of rashes on the skin. Various proposals have been made as methods to reduce the occurrence of skin rash. One method involves reducing the size of the preparation so that the portion of the skin where the rash occurs will be smaller. However, it is necessary to increase the amount of percutaneous absorption per unit area in order to accomplish this. Although various types of absorption promoters were then proposed in order to increase percutaneous absorption, due in part to the fact that absorption promoters typically have a low molecular weight, there are many cases in which they are observed to demonstrate skin irritation. In addition, there are also problems including a decrease in the adhesive strength of the resultant adhesive composition when adding large amounts of absorption promoters thereto. Thus, a patch that minimizes the occurrence of skin rash while also offering excellent percutaneous transmission and adhesive strength has not yet to be successfully provided.

Therefore, an object of the present invention is to provide a patch with minimal skin irritation and favorable percutaneous absorption by designing an adhesive having excellent compatibility with isosorbide dinitrate.

Moreover, an object of the present invention is to provide a sustained release patch with minimal skin irritation and favorable percutaneous absorption.

In addition, an object of the present invention is to provide a patch with minimal skin irritation, favorable percutaneous absorption even without using percutaneous absorption promoters, and favorable adhesive strength.

The inventors of the present invention achieved the present invention as a result of earnest research to solve the above-mentioned problems.

DISCLOSURE OF THE INVENTION

More specifically, the present invention relates to an isosorbide dinitrate-containing patch comprising an adhesive layer (A') formed on a flexible support, wherein said layer comprises an adhesive composition comprising adhesive and isosorbide dinitrate, said adhesive being composed of silicone-based adhesive (A) and polyvinyl acetate-based adhesive (B), their weight ratio being A:B=85:15 to 15:85, and the weight ratio of ISDN (C) to said adhesives (A+B) being (A+B):C=90:10 to 60:40.

Moreover, the present invention relates to a production process of an isosorbide dinitrate-containing patch comprising: laminating an adhesive layer (A') with a flexible support, wherein said adhesive layer (A') comprising an adhesive composition comprised of silicone-based adhesive (A) and polyvinyl acetate-based adhesive (B), their weight ratio being A:B=85:15 to 15:85, and not containing any isosorbide dinitrate (C) or not containing isosorbide dinitrate an adequate amount; and, dispersing isosorbide dinitrate (C) on said adhesive layer (A').

In the present invention, examples of silicone-based adhesive (A) include adhesives composed of the condensation reaction product of straight-chain dimethylpolysiloxane having a terminal silanol functional group having the two-dimensional structure indicated below in formula (I):

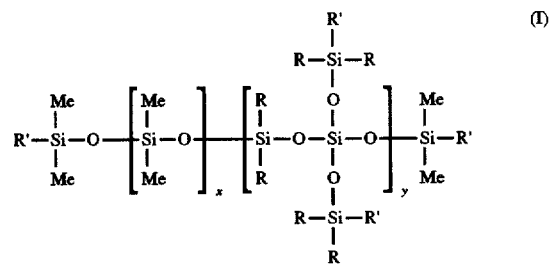

wherein
Me: —$CH_3$
R: —$CH_3$, —O—Si(Me)$_3$
R': —OH, —$CH_3$
x: 50–50,000
y: 50–50,000
(for example, a polysiloxane having a viscosity from about 100,000 to 3,000,000 cp at 25° C.) and silicate resin having a three-dimensional structure, which is shown in Pharmtech Japan 7(7), 51–55 (1991), and has excellent properties as an adhesive for percutaneous absorption preparations. Naturally, in the above-mentioned general formula, all or a portion of R and/or R' may be substituted with other alkyl groups, vinyl groups, alkoxy groups or aryl groups and so forth provided that they have almost no effect on the adhesive properties.

Specific examples of silicone-based adhesive (A) of the present invention represented with the above-mentioned formula (I) include, for example, Bio-PSA (registered trademark) 355, Bio-PSA (registered trademark) Q7-2920, Bio-PSA (registered trademark) Q7-4501 manufactured by Dow-Corning, and PSA6574 of Toshiba Silicone.

In the silicone-based adhesive (A) of the present invention, even if the chemical structure of the skeleton and substitution groups in the above-mentioned formula (I) are partially changed with conventional known groups such as carboxyl groups, alkyl groups, vinyl groups and phenyl groups, the percutaneous absorption and adhesive properties of said silicone-based adhesive (A) are practically unaffected. Thus, this type of silicone-based adhesive can be used, for example, in ordinary pharmaceutical applications. In addition, said silicone-based adhesive can be used alone or as a mixture of 2 or more types.

Examples of silicone-based adhesives (A) in the present invention preferably include adhesives represented with the above-mentioned formula (I), for example Bio-PSA355, Bio-PSAQ7-2920, Bio-PASQ7-4501 and PSA6574, and more preferably Bio-PSAQ7-4501 and PSAQ7-2920 since they are resistant to peeling, result in less pain when removed, and have a suitable degree of tackiness.

In addition, the polyvinyl acetate-based adhesive (B) in the present invention refers to, for example, vinyl acetate homopolymer, copolymers of vinyl acetate and (meth) acrylate alkyl ester and/or (meth)acrylic acid, and copolymers of vinyl acetate and vinyl ethers such as vinyl butyl ether. For example, although other components such as vinyl laurate can be incorporated, the copolymerization ratio of vinyl acetate must be at least 50% by weight of the polymer.

Here, (meth)acrylate alkyl esters are preferably alkyl esters of (meth)acrylic acid having a mean carbon number of 3 to 14, examples of which include butyl (meth)acrylate, amyl (meth)acrylate, hexyl (meth)acrylate, heptyl (meth)acrylate, octyl (meth)acrylate, nonyl (meth)acrylate, decyl (meth)acrylate and 2-ethylhexyl (meth)acrylate.

Examples of polyvinyl acetate-based adhesive (B) of the present invention preferably include copolymers of vinyl acetate and (meth)acrylate alkyl esters and/or (meth)acrylic acid, and particularly preferably copolymers of vinyl acetate and alkyl esters of (meth)acrylic acid having a mean carbon number of 3 to 14, especially, for example copolymers of 2-ethylhexyl (meth)acrylate and (meth)acrylic acid. The copolymerization ratio of the polymer in this case is such that the ratio of vinyl acetate is at least 50% by weight, preferable examples of which include those in which the copolymerization ratio of vinyl acetate to (meth)acrylate alkyl ester and/or (meth)acrylic acid is 50:50 to 90:10, and preferably 60:40 to 80:20. A copolymerization ratio of approximately 70:30 is particularly preferable.

In the present invention, a mixture system of this silicone-based adhesive (A) and polyvinyl acetate-based adhesive (B) is used. The advantages of this combination include extremely high percutaneous absorption of ISDN, and a low level of skin irritation.

As previously described, silicone-based adhesives are known to be used in ISDN-containing patches. However, with respect to mixture systems of heterogeneous types of adhesives, mixing is actually hardly ever performed with the exception of the case of rubber-based adhesives in which its properties are inherently not demonstrated unless it is mixed. In particular, there are no known patches obtained by mixing a silicone-based adhesive and polyvinyl acetate-based adhesive. This is considered to be because the solvents used for both adhesives are different, and also both are extremely different in terms of chemical structure, thus there has been no need to mix the two.

The patch of the present invention using a mixed adhesive of silicone-based adhesive (A) and polyvinyl acetate-based adhesive (B) exhibits good percutaneous absorption that is equal to or better than patches obtained by using other preferable adhesives such as acrylic-based adhesives. In addition, adhesive strength to the skin is also favorable. With respect to this point, it is thought that mixed adhesive obtained by mixing different types of adhesives form a so-called matrix-island structure, resulting in the appearance of special characteristics in adhesion with the skin and release of ISDN.

In particular, when ISDN is added to a mixture of silicone-based adhesive (A) and polyvinyl acetate-based adhesive (B), there is a specific change in percutaneous absorption, with the maximum value of percutaneous absorption being when the mixing ratio (weight ratio) of A and B is in the vicinity of approximately 30:70. Moreover, a surprising effect is demonstrated whereby the percutaneous absorption of the mixture is nearly 3 times greater than that of either adhesive alone. Even if this maximum value is not demonstrated, percutaneous absorption increases to an extent that still enables the benefits of mixing to be adequately enjoyed even when the ratio of A:B is within the range of 85:15 to 15:85.

If the ratio of A is increased beyond a ratio of A:B of 85:15, percutaneous absorption of the drug decreases, and if the ratio of B is increased beyond a ratio of A:B of 15:85, the adhesive strength of the patch decreases somewhat, thus resulting in concern over stable adhesion over a long period of time.

Namely, although the weight ratio of A:B=85:15 to 15:85 in the present invention, ratios of A:B=20:80 to 40:60 are preferable, while a ratio of A:B of approximately 30:70 is particularly preferable.

Examples of preferable combinations of adhesives (A) and (B) in this type of mixed adhesive of silicone-based adhesive (A) and polyvinyl acetate-based adhesive (B) include those in which case silicone-based adhesive (A) is an adhesive represented with the above-mentioned formula (I) and, specifically, is Bio-PSA (registered trademark) 355, Bio-PSA (registered trademark) Q7-2920 or Bio-PSA (registered trademark) Q7-4501 made by Dow-Corning, or PSA6574 made by Toshiba Silicone, and in which polyvinyl acetate-based adhesive (B) is a homopolymer of vinyl acetate, a copolymer of vinyl acetate and (meth)acrylate alkyl ester and/or (meth)acrylic acid, or a copolymer of vinyl acetate and a vinyl ether such as vinyl butyl ether, and the copolymerization ratio of vinyl acetate is at least 50% by weight, particularly a copolymer of vinyl acetate and (meth) acrylate alkyl ester and/or (meth)acrylic acid, wherein the copolymerization ratio of vinyl acetate is at least 50%, and more particularly a copolymer of vinyl acetate and an alkyl ester of (meth)acrylic acid, having a mean carbon number of 3 to 14, and (meth)acrylic acid, more specifically, a copolymer of 2-ethylhexyl (meth)acrylate and (meth)acrylic acid wherein the copolymerization ratio of vinyl acetate is at least 50%, and particularly that in which the copolymerization ratio is 60:40 to 80:20.

In the adhesive composition of the patch of the present invention, the ratio of ISDN (C) to the above-mentioned mixed adhesive is such that ISDN is blended or contained so that the relationship of the weight of ISDN (C) to the total weight of silicone-based adhesive (A) and polyvinyl acetate-based adhesive (B) ((A+B):C) being 90:10 to 60:40 is satisfied. If the ratio of ISDN (C) is less than 10, the effect of the drug is inadequate, while if it exceeds 40, the amount of crystallized ISDN in the adhesive increases causing a decrease in the adhesive strength of the resulting adhesive and a corresponding decrease in the flexibility of the patch. Moreover, even if the amount of ISDN is increased beyond 40, since the percutaneous absorption per unit area of ISDN does not increase, the availability of ISDN decreases.

In the present invention, silicone-based adhesive (A) and polyvinyl acetate-based adhesive (B) are dissolved or dispersed in a single solvent or a mixture of solvents such as ethyl acetate, hexane, chloroform, xylene, toluene, hexane, acetone or methanol. ISDN (C) is mixed into the resulting adhesive solution or dispersion, or the resulting adhesive solution or dispersion is coated on a piece of separating paper or separating film, without mixing ISDN (C) or without mixing an adequate amount of ISDN (C), so that the thickness after drying will be a prescribed thickness, namely 5–100 μm, drying the resulting paper or film, and sufficiently removing the solvent by evaporation to obtain an adhesive layer (A') that contains ISDN (C) or an adhesive layer (A') that does not contain or does not sufficiently contain ISDN (C).

In the case wherein an adhesive layer (A') containing ISDN (C) is obtained by mixing ISDN (C) into an adhesive solution, followed by coating and drying under mild conditions, a patch can be obtained by laminating said adhesive layer (A') containing ISDN (C) (corresponding to adhesive layer (d) described later) with a laminate comprising film layer (a), adhesive layer (B')(b) and fabric (c), in which ISDN being dropped into said fabric (C) in advance as necessary using a method to be described later in order to ensure an adequate content of ISDN, and consequently attaching adhesive layer (A')(d) to a flexible support, and then cutting to a desired size.

A particularly preferable patch of the present invention is obtained in the case of coating and drying an adhesive solution without mixing ISDN or a sufficient amount of ISDN into this adhesive solution. A sufficient amount refers to the amount which exhibits pharmaceutical effects.

Namely, as is commonly known, as the amount of residual solvent in the patch decreases, and more specifically, as the amount of residual solvent approaches 100 ppm or less, and preferably 50 ppm or less, the skin irritation of the patch also decreases. Thus, in order to obtain a patch having a low level of residual solvent, it is preferable to apply sufficient heat and/or allow sufficient drying time when coating and drying the solution or dispersion of adhesive on the separation film and so forth, or heat the resulting adhesive layer (A') or place it in a vacuum so as to reduce the amount of residual solvent. Since ISDN is a sublimating drug, if ISDN is contained in advance and then heated, the ISDN sublimates and results in the problem of a loss of content. However, in the case of an adhesive layer (A') that does not contain ISDN or does not sufficiently contain ISDN, it is not necessary whatsoever to take into consideration the sublimation of ISDN, thus enabling an adhesive layer (A') having a sufficiently low amount of residual solvent to be easily produced.

Thus, in the production method of a preferable patch of the present invention, an adhesive layer (A') is first obtained that does not contain ISDN or does not sufficiently contain ISDN by coating an adhesive solution or dispersion without mixing ISDN or without mixing a sufficient amount of ISDN therein, and then adhering the desired ISDN onto the adhesive layer (A') by dropping, spraying, coating or immersing in an ISDN solution, in which ISDN is dissolved at a high concentration in a highly volatile solvent such as acetone, methanol, ethanol or ethyl acetate, either directly or indirectly by means of a film, knitted fabric, woven fabric, non-woven fabric or a composite material of these. Next, said ISDN is dispersed in said adhesive layer (A') by allowing it to stand for a long time or heating and so forth to obtain a patch.

Even if the solvent used for producing an adhesive layer (A') by coating and drying and the solvent used for dissolving ISDN are the same, obtaining a patch by the method previously explained, using the solvent used to dissolve ISDN, makes it much easier to reduce the residual solvent in the patch.

In the present invention, in addition to the above-mentioned components A through C, other adhesives, including rubber-based adhesives and vinylether-based adhesives either alone or as a mixture may be used, and known absorption promoters, dissolution assistants, dispersing assistants, fillers and so forth may also be contained either alone or as a mixture as necessary in the adhesive composition provided they have no practical effect on the properties of the composition.

When using an absorption promoter, isopropyl myristate is particularly preferable as an absorption promoter. When using isopropyl myristate, it should be used in the amount of 0.01 to 5 parts by weight to 1 part by weight of ISDN (C).

In addition, examples of other absorption promoters and dispersion assistants that can be used include surfactants such as sodium lauryl sulfate, sodium dodecylbenzene sulfonate, sodium alkyldiphenylether disulfonate, dioctyl sulfo-succinate and polyoxyalkylphenylethersulfate ammonium salt; alcohols such as glycerine, diethylene glycol, propylene glycol, polyethylene glycol and higher aliphatic alcohols; dimethylsulfoxide and alkylmethyl derivatives; salicylic acid, urea, dimethylacetoamide, dimethylformamide, lanolin, allantoin, squalene, carbopore, diisopropyl adipate, pyroglutamic lauryl ester, ethyl laurate, methyl nicotinate, sorbitol and pyrolidone derivatives, such as dodecylpyrolidone, olive oil, castor oil, liquid paraffin, Vaseline, gelatin, amino acids, lactic acid, ethyl lactate, benzyl nicotinate, L-menthol, camphor and dodecylazacycloheptane-2-one. Said additives should be used in the amount of 0.05 to 5 parts by weight per 1 part by weight of ISDN.

In the patch of the present invention, the adhesive layer (A'), comprising an adhesive composition containing silicone-based adhesive (A), polyvinyl acetate-based adhesive (B) and ISDN (C) is formed on a flexible support. Film, fabric, such as knitted fabric, woven fabric or non-woven fabric, or a composite material of film and fabric can be used for said flexible support.

Examples of materials that can be used for said film or fabric include polyesters such as polyethylene terephthalate, polyolefins such as polyethylene and polypropylene, polyamides such as Nylon 6, and copolymers of ethylene and vinyl acetate. Polyester is preferable in terms of stability and safety.

In particular, in the case of using a film on the outer surface of the patch as a flexible support that is resistant to leakage of ISDN from the patch and is highly stable, when a mode is adopted in which a fabric such as knitted fabric, woven fabric or non-woven fabric is attached inside or outside of said film via an adhesive for the purpose of improving the ease of handling of the patch, the resulting patch has a high degree of stability and its handling is favorable. As explained, in order to obtain high stability and favorable handling, it is preferable that the thickness of the film be 0.5 to 10 μm, and the fabric has 8 to 100 g/m² unit area weight, and a polyester film having a thickness of 0.5 to 4.9 μm and a polyester fabric having 5 to 60 g/m² unit area weight is particularly preferable.

BEST MODE OF THE INVENTION

The following describes a particularly preferable mode of the patch of the present invention.

Namely, said patch comprises:

(a) a film layer, (b) an adhesive layer (B'), (c) fabric (d) an adhesive layer (A'), and (e) a separating film layer wherein the outermost layer is (a), and the other layers in the order of (a), (b), (c), (d) and (e) are laminated on that layer, which (e) is discarded in use.

Layer (a) is a polyester film layer having a thickness of 0.5 to 4.9 μm, and the ultra-thin polyester film developed and sold by Teijin Ltd. for use in condensers (trade name: Teijin Tetoron Film Type F) is particularly preferable for the film. Layer (b) is an adhesive layer having a thickness of about 5 to 40 μm, and is composed of, for example, a silicone-based adhesive, acrylic-based adhesive, rubber-based adhesive, polyvinyl acetate-based adhesive or an ethylene-vinyl acetate copolymer-based adhesive and so forth either alone or as a mixture. Among others, (b) is an adhesive layer having a thickness of about 10 to 25 μm and the adhesive is a rubber-based adhesive. (c) is a polyester fabric having 5 to 60 g/m² unit area weight. (d) is the adhesive layer (A') of the present invention, as described above, composed of a mixture of silicone-based adhesive (A) and polyvinyl acetate-based adhesive (B), wherein the weight ratio of A and B is 85:15 to 15:85 and the thickness is 10 to 60 μm. (e) is a polyester film-based separating film coated with a fluorine resin and having a thickness of 30 to 100 μm. Although ISDN (C) is mainly present in the adhesive layer (A')(d), it may also be present in adhesive layer (B')(b) and fabric (c).

In such a particularly preferable patch, the polyester film of film layer (a) preferably has a thickness within the range of 0.5 to 4.9 μm in terms of strength, ease of handling, skin rash and sealing. If the thickness is less than 0.5 μm, there are cases in which strength, ease of handling and so forth are inadequate, while if the thickness exceeds 4.9 μm, there are cases of problems with respect to skin retention and skin rash. A thickness of about 1.0 to 3.5 μm is particularly preferable in terms of strength, ease of handling, retention and skin rash.

In addition, although polyester having 5 to 60 g/m² unit area weight, and particularly that having 10 to 40 g/m² unit area weight, is preferable for fabric (c) in terms of skin rash and ease of handling, that having 10 to 25 g/m² unit area weight is even more preferable due to superior drug dispersion and absorption. Although there are no particular limitations on the thickness of the fibers in this case provided that a fabric having the above-mentioned unit area weight is obtained, with respect to, for example, the thickness of the fibers that compose a polyester hollow fiber fabric like that described later, fabrics having the above-mentioned unit area weight are preferable in the case of fibers of about 20 to 75 denier, examples of which include fabric having about 12 to 16 g/m² unit area weight with about 20 denier fibers, fabric having about 17 to 24 g/m² unit area weight with about 50 denier fibers, and fabric having 25 to 30 g/m² unit area weight with about 75 denier fibers. Moreover, although examples of the form of the fabric in this case include knitted fabric, woven fabric and non-woven fabric, knitted fabric is particularly preferable.

Preferable examples of combinations of these components (a) through (d) include those in which (a) is a polyester film having a thickness of about 1.0 to 3.5 μm, (b) is an adhesive layer composed of a rubber-based adhesive having a thickness of about 10 to 25 μm, (c) is a polyester fabric having 10 to 40 g/m² unit area weight, and particularly 10 to 25 g/m², and particularly a fabric that is a woven fabric having about 12 to 16 g/m² unit area weight composed of 20 denier polyester fibers, and (d) is the above-mentioned mixed adhesive layer (A') having a thickness of about 25 to 45 μm.

In the manufacturing of said preferable mode of the patch of the present invention, an adhesive layer (B')(b) not sufficiently containing ISDN and an adhesive layer (A')(d) are manufactured, a laminate is produced by adhering film layer (a) and fabric (c) via adhesive layer (B')(b), ISDN dissolved in a solvent such as acetone is incorporated into the fabric portion of said laminate by dropping, spraying or immersion, after which the ISDN solvent is removed by evaporation, and then adhesive layer (A')(d) is pressed. The patch obtained in this manner is provided with separating film layer (e).

ISDN can be adequately dispersed in adhesive layer (A')(d) by allowing the patch obtained in the above manner to stand for a long time or by heating. Although ISDN-containing patches are normally used after cutting to a size of 10–100 cm², said cutting may be performed before or after heating.

EXAMPLES

The following provides a more detailed explanation of the present invention through examples. Parts, percentages and ratios in the examples are all based on weight.

The measurement method of blood ISDN concentration, and preparation of the polyvinyl acetate-based adhesive and fabric sample used in the examples are as indicated below.

(1) Measurement Method of Blood ISDN Concentration

After separating the plasma from 1 ml of sampled whole blood, ISDN is extracted using 4 ml of n-hexane followed by concentration and the addition of 100 μl of ethyl acetate to the concentrate to obtain the sample. The amount of ISDN in the sample is assayed by GC-ECD.

(2) Preparation of Polyvinyl Acetate-Based-Adhesive

Copolymers composed of 2-ethylhexyl acrylate and so forth were used in addition to vinyl acetate (Wako Pure Chemical Industries Ltd.). This polymer was synthesized according to the following method.

Namely, 70 parts of vinyl acetate, 27 parts of 2-ethylhexyl acrylate, 3 parts of acrylic acid, 1 part of benzoyl peroxide and 150 parts of ethyl acetate were charged into a reaction vessel equipped with a reflux condenser and stirrer. Polymerization was continued for 12 hours while slowly stirring at 60° C. under a nitrogen. The polymerization conversion rate was 99.9%. 250 parts of ethyl acetate were added to the resulting polymer solution followed by adjustment of the solid concentration to about 20% to obtain a polyvinyl acetate-based adhesive solution.

(3) Preparation of Fabric Sample 297 parts of dimethyl terephthalate, 265 parts of ethylene glycol, 53 parts of sodium 3,5-di(carbomethoxy) benzene sulfonate (11.7 mol % to dimethyl terephthalate), 0.084 parts of manganese acetate 4 hydrates and 1.22 parts of sodium acetate 3 hydrates were placed in a glass flask equipped with a fractionating column. After performing transesterification in accordance with the usual method and distilling off the theoretical amount of methanol, the reaction product was placed in flask for condensation polymerization equipped with a fractionating column followed by the addition of stabilizer in the form of 0.090 parts of a 56% aqueous solution of orthophosphoric acid and condensation polymerization catalyst in the form of 0.135 parts of antimony trioxide. After reacting at 275° C. for 20 minutes under normal pressure and then for 15 minutes under reduced pressure of 30 mmHg, the reaction was continued for 100 minutes under high vacuum. The final internal pressure was 0.39 mmHg, the intrinsic viscosity of the resulting copolymer was 0.402, and the softening point was around 200° C. Following completion of the reaction, the copolymer was formed into chips in accordance with a usual process.

After mixing 15 parts of these polymer chips with 85 parts of polyethylene terephthalate chips having a intrinsic viscosity of 0.640 in a Nauta Mixer (Hosokawa Ironworks) for 5 minutes, the mixture was dried under a nitrogen for 2 hours at 110° C. and then for 7 hours at 150° C. followed by forming into chips by kneading and mixing at 285° C. using a twin-screw extruder. The intrinsic viscosity of these chips was 0.535, and the softening point was 261° C.

These chips were dried in accordance with a usual manner and then spun in accordance with a usual method using a spinneret having an arc-shaped opening in which two circular slits measuring 0.05 mm wide and 0.6 mm in diameter were closed to produce a hollow fiber having a ratio of outer diameter to inner diameter of 2:1 (hollow rate: 25%). The resulting hollow fiber had fine pores dispersed over the entire cross-sectional surface of said hollow fiber and arranged in the direction of the fiber. At least a portion of said fine pores were connected to the hollow portion of the fiber. The yarn was a 300 denier/24 filaments, and was drawn to an elongation factor of 4.2 times in accordance with a usual manner to obtain a multifilament yarn of 71 denier/24 filaments. A single filament of this multifilament yarn had a diameter of 11 μm.

This multifilament yarn was formed into a Merrius knitted fabric, and, after scouring and drying in accordance with routine methods, the fabric was treated with 1% aqueous caustic soda at boiling temperature for 2 hours to obtain a knitted fabric having an alkaline loss rate of 20%. The resulting knitted fabric was drawn by 1.5 times in the longitudinal direction and heat set by applying heat for 1 minute at 100° C. to obtain a knitted fabric having 17 g/m² unit area weight, namely the fabric sample.

Examples 1, 3 and 4 and Comparative Examples 2 and 3

Bio-PSA (registered trademark) 355 (solid portion: 18.5%) manufactured by Dow-Corning was used for silicone-based adhesive (A), while the solution obtained in (2) above was used for polyvinyl acetate-based adhesive (B).

The mixing ratio of silicone-based adhesive (A) and polyvinyl acetate-based adhesive (B) was changed as described in Table 1, and both components were mixed well to obtain a mixed dope. Two types of adhesive layers were then obtained having thicknesses after drying on a fluorine-based separating film of 15 μm (adhesive layer (B')(b)) and 40 μm (adhesive layer (A')(d)) with respect to the respective levels.

Using a 2.5 μm thick polyethylene terephthalate film (Teijin Tetoron Film Type F) for film (a), adhesive layer (b) was first pressed onto film (a), and the fabric sample (c) was pressed onto the free surface of adhesive layer (B')(b). Next, an acetone solution of ISDN (C) was continuously dropped onto the free surface of the fabric sample so that the amount of ISDN (C) would be 8 g per 1 m² of the fabric sample. After evaporating the acetone by air drying, adhesive layer (A')(d) was pressed onto the free surface of said fabric to obtain a laminate. At this time, a separating film coated with a white, fluorine-based separating agent having a thickness of 50 μm was attached to the side on which adhesive layer (A')(d) was not pressed onto the fabric. After cutting to a size of about 7 cm×7 cm (7.1 cm×7.1 cm), the resulting laminate was heated at 65° C.

A preparation for animal testing having a size of 10 cm² was made from the preparation obtained in this manner, and was applied to the shaved backs of hairless rats having a mean body weight of 200 g (n=3). Blood samples were collected before application, 5 hours after application and 24 hours after application. The ISDN concentrations in the blood of each sample were measured and Cmax and AUC values were calculated from the resulting blood concentrations. In addition, the quality of adherence to the skin was also investigated. Those results are shown in Table 1. In the table, PVAC means polyvinyl acetate.

Examples 2 and 5

With the exception of using a rubber-based adhesive layer having a thickness of 15 μm as an adhesive layer (B')(b), testing was performed in the same manner as Examples 1, 3 and 4. Those results are also shown in Table 1.

Comparative Example 1

With the exception of using an adhesive in which PVAC-based adhesive was not mixed as an adhesive layer (A')(d), testing was performed in the same manner as Examples 1, 3 and 4. Those results are also shown in Table 1.

Comparative Example 4

With the exception of using an adhesive in which silicone-based adhesive was not mixed as an adhesive layer (A')(d), testing was performed in the same manner as Examples 1, 3 and 4. Those results are also shown in Table 1.

Comparative Example 5

With the exception of using acrylic-based adhesive layers having thicknesses of 15 μm and 40 μm as an adhesive layer (B')(b) and a pressure-sensitive adhesive layer (A')(d), respectively, testing was performed in the same manner as Examples 1, 3 and 4. Those results are also shown in Table 1.

Furthermore, the acrylic-based adhesive was synthesized in accordance with the following method. 90 parts of 2-ethylhexyl acrylate, 7 parts of methyl methacrylate, 3 parts of acrylic acid, 1 part of benzoyl peroxide and 100 parts of ethyl acetate were charged into a reaction vessel equipped with a reflux condenser and stirrer. Polymerization was continued for 12 hours with slowly stirring at 60° C. under a nitrogen. The polymerization conversion rate was 99.9%. 300 parts of ethyl acetate were added to the resulting polymer solution followed by adjustment of the solid concentration to about 20%.

TABLE 1

| Mixing Ratio of Adhesive of Adhesive Layer | | Blood Pharmacokinetics | | |
|---|---|---|---|---|
| Silicone-Based Adhesive (A) | PVAc-Based Adhesive (B) | AUC (ng · hr/ml) | Cmax (ng/ml) | Quality Adherence to Skin |
| Comp. Ex. 1 | 100 | 0 | 1,274 | 88 | Good adherence, no skin irritation |
| Comp. Ex. 2 | 90 | 10 | 1,371 | 99 | Same as above |
| Ex. 1 | 85 | 15 | 1,523 | 101 | Same as above |
| Ex. 2* | 70 | 30 | 3,003 | 217 | Same as above |
| Ex. 3 | 50 | 50 | 3,674 | 255 | Same as above |
| Ex. 4 | 30 | 70 | 3,681 | 259 | Same as above |
| Ex. 5* | 30 | 70 | 3,695 | 260 | Same as above |
| Comp. Ex. 3 | 10 | 90 | 1,417 | 93 | No skin irritation, but weak adherence, problem with practical use |
| Comp. Ex. 4 | 0 | 100 | 1,159 | 72 | Same as above |
| Comp. Ex. 5 | Acrylic-based adhesive | | 1,472 | 98 | Good adherence, somewhat strong skin irritation |

*Rubber based adhesive layer was used for adhesive layer (B') (b). The same types of adhesives were used for adhesive layer (B') (b) and adhesive layer (A') (d) for others.

It can be understood from Table 1 that, in the case of the patch using a mixed adhesive of the present invention, and particularly when the mixing ratio of silicone-based adhesive (A) and polyvinyl acetate-based adhesive (B) was about 50:50 to 30:70, adherence with the skin was favorable, there was no occurrence of skin rash, and excellent blood pharmacokinetics were exhibited.

Examples 6 and 7

With the exception of using a polyethylene terephthalate film having a thickness of 1.7 μm (Teijin Tetoron Film Type F, etc.) as film (a), a rubber-based adhesive having a thickness of 15 μm as adhesive layer (b), a mixed adhesive of silicone-based adhesive (A) and polyvinyl acetate-based adhesive (B) (the polyvinyl acetate-based adhesive solution described in the above-mentioned section (2) was used as the polyvinyl acetate-based adhesive) having a thickness of 30 μm in Example 6 and 25 μm in Example 7 as an adhesive layer (A')(d), and using a fabric sample obtained from a knitted fabric having a fiber thickness of 20 denier and 14 g/m² unit area weight using the same method as that described in the above-mentioned section (3) as fabric (C), 7.1 cm×7.1 cm patches (Examples 6 and 7) described in Table 2 were obtained in the same manner as Example 1.

The AUC values of these patches were measured in the same manner as Example 1, and are shown in Table 2. The results of evaluating skin irritation are also shown in Table 2.

TABLE 2

| Ex. No. | Mixing Ratio of Adhesive of Adhesive Layer | | AUC (ng · hr/ml) | Skin Irritation and Adherence |
|---|---|---|---|---|
| | Silicone-Based Adhesive (A) | PVAc-Based Adhesive (B) | | |
| 6 | 30 | 70 | 3.520 | No skin irritation, good adherence |
| 7 | 30 | 70 | 3.632 | No skin irritation, good adherence |

Examples 8 and 9

Patches (Examples 8 and 9) were obtained in a similar manner as in Example 1 using a polyethylene terephthalate film (Teijin Tetoron Film Type F, etc.) having a thickness of 2.5 μm as film (a), a rubber-based adhesive having a thickness of 30 μm as adhesive layer (b), a mixed adhesive of silicone-based adhesive (A) and polyvinyl acetate-based adhesive (B) having a thickness of 30 μm as adhesive layer (d) (wherein, the polyvinyl acetate-based adhesive was composed from ingredients described in Table 3), and a fabric sample obtained from a knitted fabric having a fiber thickness of 50 denier and 20 g/m² unit area weight as fabric (c).

The AUC values of these patches were measured in the same manner as Example 1, and those results are shown in Table 3.

TABLE 3

| Ex. No. | Mixing Ratio of Adhesive of Adhesive Layer | | Composition of Adhesive Layer (d) 2EHA/VA/ AA/VL | AUC (ng · hr/ml) | Skin Irritation and Adherence |
|---|---|---|---|---|---|
| | Silicone-Based Adhesive | PVAc-Based Adhesive | | | |
| 9 | 40 | 60 | 37.5/ 60.0/ 2.5/ 0 | 3.304 | No skin irritation, good adherence |
| 9 | 40 | 60 | 37.5/ 50.0/ 2.5/ 10.0 | 3.472 | No skin irritation, good adherence |

2EHA: 2-ethylhexyl acrylate
VA: Vinyl acetate
AA: Acrylic acid
VL: Vinyl laurate

We claim:

1. An isosorbide dinitrate-containing patch comprising: an adhesive layer (A') formed on a flexible support, wherein said layer comprises an adhesive composition comprising adhesive and isosorbide dinitrate (ISDN), said adhesive being composed of silicone-based adhesive (A) and polyvinyl acetate-based adhesive (B), their weight ratio being A:B=85:15 to 15:85, and the weight ratio of ISDN (C) to said pressure-sensitive adhesives (A+B) being (A+B):C= 90:10 to 60:40.

2. An isosorbide dinitrate-containing patch according to claim 1 wherein the weight ratio of said adhesives is A:B=20:80 to 40:60.

3. An isosorbide dinitrate-containing patch according to claim 1 wherein said silicone-based adhesive (A) is an adhesive represented by the following formula (1):

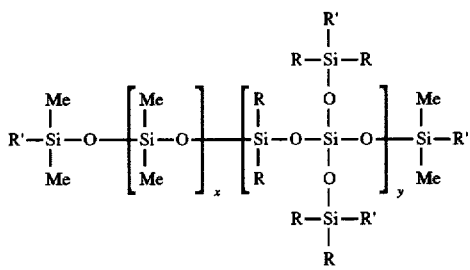

wherein:
Me: —CH$_3$
R: —CH$_3$, —O—Si(Me)$_3$
R': —OH, —CH$_3$
x: 50–50,000
y: 50–50,000.

4. An isosorbide dinitrate-containing patch according to claim 1 wherein said polyvinyl acetate-based adhesive (B) is a copolymer of vinyl acetate and (meth)acrylate alkyl ester and/or (meth)acrylic acid, and the copolymerization ratio of vinyl acetate is at least 50% by weight.

5. An isosorbide dinitrate-containing patch according to any of claims 1 to 3 wherein said polyvinyl acetate-based adhesive (B) is an adhesive wherein the copolymerization ratio of vinyl acetate to 2-ethylhexyl (meth)acrylate and (meth)acrylic acid is 60:40 to 80:20.

6. An isosorbide dinitrate-containing patch according to any of claims 1 to 4 wherein said flexible support is composed of:
(a) a film layer
(b) an adhesive layer (B'), and
(c) a fabric,
wherein the outermost layer is (a) and said flexible support is laminated in the order of (a), (b) and (c) and wherein said adhesive layer (A) is located on the fabric layer (c) side of said flexible support.

7. An isosorbide dinitrate-containing patch according to any of claims 1 to 4 wherein said adhesive layer (A') has a thickness of 10 to 60 µm.

8. An isosorbide dinitrate-containing patch according to claim 6 wherein said film layer has a thickness of 0.5 to 10 µm, and is composed of polyester, polyolefin, polyamide and/or ethylene-vinyl acetate copolymer.

9. An isosorbide dinitrate-containing patch according to claim 6 wherein said film layer is a polyester film having a thickness of 0.5 to 4.9 µm.

10. An isosorbide dinitrate-containing patch according to claim 6 wherein said adhesive layer (B') has a thickness of 5 to 40 µm, and comprises silicone-based adhesive, acrylic-based adhesive, rubber-based adhesive, polyvinyl acetate-based adhesive, ethylene-vinyl acetate-based adhesive and/or their combination.

11. An isosorbide dinitrate-containing patch according to claim 6 wherein said adhesive layer (B') is a rubber-based adhesive having a thickness of 10 to 25 µm.

12. An isosorbide dinitrate-containing patch according to claim 6 wherein said fabric layer has 8 to 100 g/m$^2$ unit area weight, and is composed of polyester, polyolefin, polyamide and/or ethylene-vinyl acetate copolymer.

13. An isosorbide dinitrate-containing patch according to claim 6 wherein said fabric layer is polyester having 5 to 60 g/m$^2$ unit area weight.

14. An isosorbide dinitrate-containing patch according to claim 6 wherein said adhesive layer (A') has a thickness of 10 to 60 µm, said film layer is polyester film having a thickness of 0.5 to 4.9 µm, said adhesive layer (B') is a rubber-based adhesive having a thickness of 10 to 25 µm, and said fabric layer is polyester having 5 to 60 g/m$^2$ unit area weight.

15. A production process of an isosorbide dinitrate-containing patch comprising: laminating an adhesive layer (A') with a flexible support, wherein said adhesive layer (A') comprising an adhesive composition comprised of silicone-based adhesive (A) and polyvinyl acetate-based adhesive (B), their weight ratio being A:B=85:15 to 15:85, and not containing any isosorbide dinitrate (C) or not containing isosorbide dinitrate in an adequate amount; and, dispersing isosorbide dinitrate (C) on said adhesive layer (A').

* * * * *